United States Patent [19]

Braunwarth

[11] 4,110,358
[45] Aug. 29, 1978

[54] AMPHOLYTIC QUATERNARY AMMONIUM COMPOUNDS AND METHODS FOR THEIR PREPARATION

[75] Inventor: John B. Braunwarth, Janesville, Wis.

[73] Assignee: Armstrong Chemical Co., Inc., Janesville, Wis.

[21] Appl. No.: 688,950

[22] Filed: May 24, 1976

[51] Int. Cl.$^2$ .............................................. C09F 5/00
[52] U.S. Cl. ................. 260/404.5; 260/404; 260/465.5 R; 260/534 M; 260/567.6 M; 260/601 R; 560/156; 560/179
[58] Field of Search ...... 260/404, 404.5 Q, 404.5 EO, 260/567.6 M, 534 M, 465.5 R, 601 R; 560/156, 179

[56] References Cited

U.S. PATENT DOCUMENTS

| | | | |
|---|---|---|---|
| 2,468,012 | 4/1949 | Isbell | 260/482 X |
| 2,897,170 | 7/1959 | Gruber | 260/567.6 M |
| 3,790,606 | 2/1974 | Sellet | 260/404.5 Q |
| 3,912,771 | 10/1975 | Kuhn et al. | 260/404.5 Q |
| 3,933,871 | 1/1976 | Armstrong | 260/404.5 Q |

*Primary Examiner*—Winston A. Douglas
*Assistant Examiner*—John F. Niebling
*Attorney, Agent, or Firm*—Carl C. Batz

[57] ABSTRACT

Ampholytic quaternary ammonium compounds according to the formula:

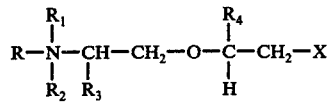

where R, $R_1$ and $R_2$ each is an alkyl group containing a carbon chain of from 1 to 22 carbon atoms, $R_3$ is H, $CH_3$ or $CH_3CH_2$, $R_4$ is H or $CH_3$, and X is COOH, CN, CHO, or $COOCH_3$ and methods for preparing such compounds wherein a tertiary amine is reacted with an $\alpha,\beta$ unsaturated compound to produce an intermediate reaction product and this intermediate reaction product is reacted with an alkylene oxide to produce the ampholytic quaternary ammonium compound.

21 Claims, No Drawings

AMPHOLYTIC QUATERNARY AMMONIUM COMPOUNDS AND METHODS FOR THEIR PREPARATION

This invention relates to quaternary ammonium comounds, particularly such compounds which are ampholytic in character, and to methods for their preparation.

BACKGROUND

It is known that tertiary amine salts may be treated with ethylene oxide to yield the analogous quaternary ammonium compound (British patent specification No. 448,251 and U.S. Pat. No. 2,897,170). It is also known that ampholytic quaternary ammonium compounds can be produced from tertiary ammonium compounds by treatment with monochloroacetic acid or sodium monochloroacetate. Also, ampholytic compounds derived from imidazolines are marketed under the trademark Miranol. These compounds and the process of preparing them are set forth in U.S. Pat. No. 2,528,378.

The reactions set forth in U.S. Pat. No. 2,528,378 are time consuming, requiring several hours to go to completion. Also, sodium chloride formed as a by-product must be removed if a salt free product is desired and this requires expensive purification steps.

Ampholytic compounds can be produced by reacting primary or secondary amines with an acrylic ester and hydrolyzing the resulting aminocarboxylic ester (U.S. Pat. No. 2,468,012). But these compounds are not quaternary ammonium compounds and reaction of an acrylic ester with tertiary amines does not occur under the same conditions.

Cyanoethylation of primary or secondary amines also occurs readily, but again no such reaction occurs with a tertiary amine, and quaternary ammonium compounds are not produced.

Cyanoethylation reactions of the following types do occur with tertiary amines:

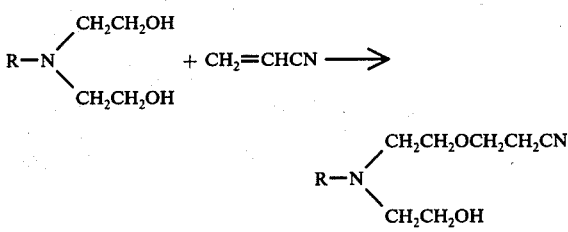

But, again, quaternary ammonium compounds are not produced.

SUMMARY

In the light of the prior knowledge in this field as above discussed one would not expect that by reacting a tertiary amine with an $\alpha,\beta$ unsaturated compound, such as acrylic acid, and an alkylene oxide, such as ethylene oxide, an ampholytic quaternary ammonium compound would be produced, but I have discovered that such reaction does occur and that by this reaction novel and useful compounds can be prepared. These compounds have good foaming characteristics and can be used in the formulation of cleaning compositions, shaving creams, and the like.

DESCRIPTION

As above indicated, the starting materials for my reaction are a tertiary amine, an $\alpha,\beta$ unsaturated compound and an alkylene oxide.

The tertiary amine may be any tertiary amine of the general formula

wherein each of the alkyl groups $R,-R_1$ and $R_2$ contain a carbon chain of 1 or more carbon atoms. The shortest chain is represented by $CH_3$ and the length of chain is limited only by practical utility at about 22 carbon atoms. This alkyl group may stand along or as a part of a more complex group to which it may be bonded. By the term "alkyl" we include both the saturated group and the unsaturated group which has sometimes been called alkylene. These alkyl groups may be derived from any source such as from tallow, coconut oil, soybean oil, etc. The alkyl groups so derived have the same carbon chain lengths as are found in their respective sources, and for convenience they are herein called "tallow", "coco", "soya", as the case may be. I prefer that at least one of the alkyl groups $R$, $R_1$ or $R_2$, contain a carbon chain of from 10 to 18 carbon atoms.

Specific examples of tertiary amines which may be used are:

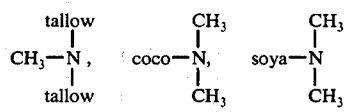

The alkylene oxides which may be used as starting materials contain from 2 to 4 carbon atoms, examples of which are:

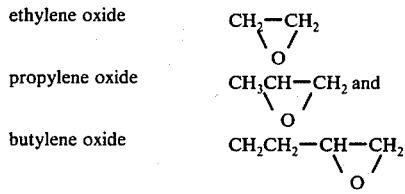

The $\alpha,\beta$ unsaturated compounds include any compound having $\alpha,\beta$ unsaturation and which contains activating groups such as COOH,—CHO,—COOR-,—CN, etc, sometimes referred to as conjugated systems. Examples of the $\alpha,\beta$ unsaturated acids are acrylic acid, crotonic acid and maleic acid; also acrylonitrile; styrene, crotonaldehyde, ethyl acrylate, crotonyl alcohol, butadiene and methyl maleate.

The amine, $\alpha,\beta$ unsaturated compound and the alkylene oxide starting materials are used in a 1 to 1 to 1 molar ratio, or nearly so. Greater or lesser proportions of any one reactant may be used but will result in some unreacted chemical in the resulting product.

In conducting the reaction the tertiary amine and the $\alpha,\beta$ unsaturated compound may be placed in a reactor equipped for stirring and the reactants mixed in the reactor. This reaction results in an intermediate compound which, when an $\alpha,\beta$ unsaturated acid is used, is usually a salt. Then the reactor is closed and the alkylene oxide is added while continuing the mixing. Pressure is not required and the closed reactor is used to retain the alkylene oxide. Specific temperatures are not essential to the reactant, but a temperature in the range of from 140° F to 230° F is preferred. There is some indication that the reaction is exothermic.

Also, it is preferably that the reaction be conducted in the presence of a solvent such as water, isopropanol, methanol, ethanol or hexylene glycol, but a solvent is not essential to the process.

The reaction is usually complete from within 30 minutes to 6 hours.

The structural formulae describing my reactions may be demonstrated as follows: (For simplicity, I refer to the reactions using acrylic acid and ethylene oxide).

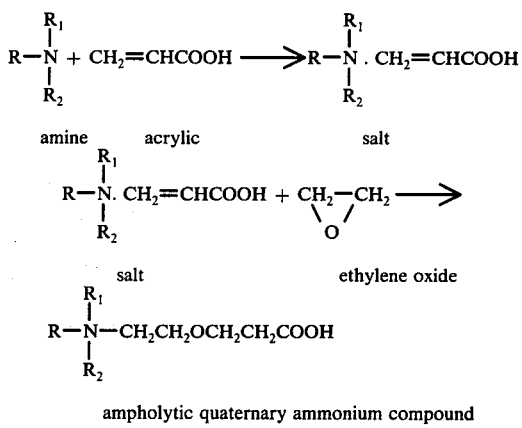

ampholytic quaternary ammonium compound

The following specific examples demonstrate the preparation of various specific ampholytic quaternary ammonium compounds in accordance with my invention:

EXAMPLE I 90 grams of glacial acrylic acid, 394.8 grams of tertiary amine and 1,000 grams of tap water were charged into a reactor equipped with power stirring. The tertiary amine has been prepared by reacting dimethyl amino propyl amine and coconut oil. The tertiary amine reaction product so prepared has the tradename "Amine CPA". The reactor was then closed and 60 grams of ethylene oxide added with continued stirring at a temperature of about 150° F for about 4 hours.

Analysis of the product showed a solids content of 35.3 percent, a color of Gardner 4, a pH of 7.0 and an activity content, based on the molecular weight of 445, of 22.6 percent. The product was crystal clear in water and soluble in 20 percent potassium hydroxide solution and in concentrated hydrochloric acid and in concentrated sulfuric acid.

EXAMPLE II 161.7 grams, which amounted to about half a mole of "Amine CPA", 26 grams of acrylonitrile and about 205 grams of distilled water were placed in a 1 liter 3 necked flask equipped with a mechanical stirrer, a reflux condenser and a thermometer. After stirring it was noted that the mixture was not pink to phenolphalein. The flask was closed and 46.7 grams of ethylene oxide added with continued stirring. The product turned orange to phenolphthalein and with additional phenolphthalein the reaction mixture became a vivid violet. The temperature went rapidly to 160° C and began to gel even with water present. 450 more grams of water was added. A sample was analyzed and, based on quaternary analysis, showed to be 26.6 precent active.

EXAMPLE III 535 grams of methyl dihydrogenated tallow amine, 72 grams of acrylic acid and 72 grams of water were charged into a reactor equipped with power stirring equipment. After mixing the charge was allowed to stand overnight. 500 grams of additional water was added. The reactor was sealed and 44 grams of ethylene oxide at 180° F to 200° F. The ethylene oxide addition appeared to stop sharply at 44 grams. When 1 mole of ethylene oxide had been added, 7.1 percent quaternary ammonium compound had been formed. In 30 minutes when 1.2 moles of ethylene oxide had been added about 13 percent quaternary ammonium compound had been formed. At about 1 hour, when 1.4 moles of ethylene oxide had been added, 15.4 percent quaternary ammonium compound had been formed, and after 24 hours, 20.3 percent quaternary ammonium compound had been formed. Solids content of the reaction product was found to be 43.8 percent.

EXAMPLE IV

Reaction of Dimethylaminopropylene Cocoamide (CPA), Ethylene Oxide and Acrylic Acid The CPA, the acrylic acid and water were charged into a 2 liter stainless steel Parr reactor and were mixed to form a homogeneous mixture. The autoclave was sealed, heated to 150° F, and ethylene oxide added. After mixing for about 1½ hours the reaction mixture was cut back to about 25 to 35 percent active quaternary ammonium compound by the addition of water.

The reaction product was a light yellow liquid with solids of 30 wt. percent, pH of seven and had a mild odor. Salt content was 0.0 percent, density was 8 lbs/gallon, and specific gravity was 0.96. Tests showed the product to be soluble in water, alcohols, 35 percent potassium hydroxide, 25 percent sodium hydroxide, concentrated sulfuric acid, 30 percent sodium metasilicate, nonionics, quaternary amine, coconut alkanolamides, and sodium lauryl ether sulfate. Solubility properties show that the product is ampholytic in character.

Data as to further runs using dimethyl aminopropylene cocoamide (CPA), ethylene oxide and acrylic acid, are given in Table I as follows:

TABLE I

| REACTIONS OF DIMETHYL AMINOPROPYLENE COCOAMIDE (CPA), ETHYLENE OXIDE AND ACRYLIC ACID | | | | | | | |
|---|---|---|---|---|---|---|---|
| Experiment No.: | B11-30 | B11-32 | B11-40A | -B11-40B | B11-42 | LJA-101 | B11-49 |
| Reactant Charges: | | | | | | | |
| | Wt.,G. (Moles) | | | | | | |
| CPA | 435.3(1.35) | 547.2(2.0) | 323.5(1.0) | 325.9(1.01) | 325.9(1.01) | 330(1.02) | 325.9(1.01) |
| Acrylic Acid | 96.8(1.41) | 136.8(2.0) | 70.2(1.02) | 66.3(0.97) | 66.3(0.97) | 76(1.11) | 66.3(0.97) |
| Ethylene Oxide | 85.0(1.93) | 85.0(1.93) | 90.0(2.04) | 80.0(1.82) | 53.0(1.2) | 50(1.14) | 60.0(1.36) |

TABLE I-continued
REACTIONS OF DIMETHYL AMINOPROPYLENE COCOAMIDE (CPA), ETHYLENE OXIDE AND ACRYLIC ACID

| Experiment No.: | B11-30 | B11-32 | B11-40A | -B11-40B | B11-42 | LJA-101 | B11-49 |
|---|---|---|---|---|---|---|---|
| Isopropanol | — | 40 | 20 | 20 | 20 | — | — |
| $H_2O$ Solids Adjustment of Product | — | — | — | — | — | 800 | 735 |
| $H_2O$ Reactant Mole Ratio | 700 | 500 | 642 | 642 | 735 | — | — |
| E.O./CPA | 1.43 | 0.97 | 2.04 | 1.80 | 1.20 | 1.11 | 1.34 |
| A.A./CPA | 1.04 | 1.00 | 1.02 | 0.96 | 0.96 | 1.08 | 0.96 |
| Ethylene Oxide Addition Temperature ° F | 180–200 | 180–200 | 200–220 | 200–220 | 180–220 | 140–150 | 180–200 |
| Product Color | Yellow | Yellow | Red | Red | Yellow | Yellow | Yellow |

Data as to further runs using methyl dihydrogenated tallow amine, acrylic acid and ethylene oxide, are given in Table II as follows:

TABLE II
METHYL DIHYDROGENATED TALLOW AMINE, ACRYLIC ACID AND ETHYLENE OXIDE REACTIONS

| Experiment Reactant Charges | LJA-102 Wt.G. (Moles) | LJA-103 Wt.g. (Moles) |
|---|---|---|
| Methyl dihydrogenated tallow amine | 700 (1.33) | 700 (1.33) |
| Acrylic Acid | 98 (1.44) | 98 (1.43) |
| Ethylene Oxide | 70 (1.59) | 70 (1.59) |
| Isopropanol | 180 | — |
| Water | 90 | 60 |
| Solids | 75 | 90 |
| Reaction Temp., ° F. | 140–150 | 140–150 |
| Run Time, Hr. | 1.5 | 1.5 |
| EO/Amine | 1.2 | 1.2 |
| AA/Amine | 1.08 | 1.08 |

While in the foregoing description only certain of my improvements have been specifically set forth, it will be apparent to those skilled in this art that all such specific compounds falling within the generic designation herein given may be made and that many changes may be made both as to the compounds and the particular processes for their preparation, all such modifications and changes being within the spirit of the invention as herein set forth and the scope of the appended claims.

I claim:

1. An ampholytic quaternary ammonium compound having the structure:

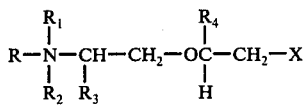

where R, $R_1$ and $R_2$ each is an alkyl group containing a carbon chain of from 1 to 22 carbon atoms, $R_3$ is H, $CH_3$ or $CH_3CH_2$, $R_4$ is H or $CH_3$, and X is COOH, CN, CHO, or $COOCH_3$.

2. A compound as set forth in claim 1 where R is an alkyl group derived from coconut oil and $R_1$ and $R_2$ are each $CH_3$.

3. A compound as set forth in claim 1 where R is $CH_3$ and $R_1$ and $R_2$ are each an alkyl group derived from tallow.

4. A compound as set forth in claim 1 where $R_3$ is H.

5. A compound as set forth in claim 1 where $R_4$ is H.

6. A compound as set forth in claim 1 where X is COOH.

7. A compound as set forth in claim 1 where X is CN.

8. A compound as set forth in claim 1 where X is COO $CH_3$.

9. A process for preparing an ampholytic compound comprising mixing a tertiary amine having the formula

where R, $R_1$ and $R_2$ each is alkyl and has from 1–22 carbon atoms, with an $\alpha$, $\beta$ unsaturated compound which has a conjugated system to produce an intermediate reaction product, and mixing with said intermediate product an alkaline oxide to produce an ampholytic quaternary ammonium compound.

10. A process as set forth in claim 9 in which said $\alpha,\beta$ unsaturated compound is acrylic acid.

11. A process as set forth in claim 9 in which said $\alpha,\beta$ unsaturated compound is crotonic acid.

12. A process as set forth in claim 9 in which said $\alpha,\beta$ unsaturated compound is maleic acid.

13. A process as set forth in claim 9 in which one of the alkyl groups attached to the nitrogen atom of said amine has a carbon chain length of from 10 to 14 carbon atoms.

14. A process as set forth in claim 9 in which said alkylene oxide is ethylene oxide.

15. A process as set forth in claim 9 in which said alkylene oxide is propylene oxide.

16. A process as set forth in claim 9 in which said amine, said $\alpha,\beta$ unsaturated compound and said alkylene oxide are in the molar proportions of about one to one to one.

17. A process as set forth in claim 9 in which said $\alpha,\beta$ unsaturated compound is acrylonitrile.

18. A process as set forth in claim 9 in which said alkylene oxide is stirred with said intermediate reaction product at a temperature of about 140° F to 230° F.

19. A process as set forth in claim 9 in which a solvent is present when said alkylene oxide is mixed with said intermediate reaction product.

20. A process as set forth in claim 19 in which said solvent is water.

21. An ampholytic quaternary ammonium compound having the structure:

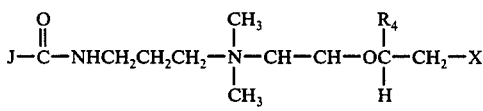

where
$R_3$ is H, $CH_3$ or $CH_3CH_2$,
$R_4$ is H or $CH_3$,
X is COOH, CN, CHO or $COOCH_3$, and
J is an alkyl group having a chain of 1–22 carbon atoms and is derived from coconut oil.

* * * * *